US012778900B2

(12) United States Patent
Sharma

(10) Patent No.: US 12,778,900 B2
(45) Date of Patent: Nov. 3, 2026

(54) DELMOPINOL AND DELMOPINOL SALT CONTAINING NANOPARTICLES AND USES THEREOF

(71) Applicant: You First Services, Inc., Buffalo, NY (US)

(72) Inventor: Satish Sharma, Buffalo, NY (US)

(73) Assignee: You First Services, Inc., Buffalo, NY (US)

( * ) Notice: Subject to any disclaimer, the term of this patent is extended or adjusted under 35 U.S.C. 154(b) by 205 days.

(21) Appl. No.: 18/850,002

(22) PCT Filed: Mar. 23, 2023

(86) PCT No.: PCT/US2023/064862
§ 371 (c)(1),
(2) Date: Sep. 23, 2024

(87) PCT Pub. No.: WO2023/183872
PCT Pub. Date: Sep. 28, 2023

(65) Prior Publication Data

US 2025/0205170 A1 Jun. 26, 2025

Related U.S. Application Data

(60) Provisional application No. 63/322,901, filed on Mar. 23, 2022.

(51) Int. Cl.

| | |
|---|---|
| ***A61K 9/51*** | (2006.01) |
| ***A61K 31/5375*** | (2006.01) |
| ***A61K 45/06*** | (2006.01) |

(52) U.S. Cl.
CPC .......... *A61K 9/5153* (2013.01); *A61K 9/5161* (2013.01); *A61K 31/5375* (2013.01); *A61K 45/06* (2013.01)

(58) Field of Classification Search
CPC ................ A61K 9/5153; A61K 9/5161; A61K 31/5375; A61K 45/06; A61K 2300/00
See application file for complete search history.

(56) References Cited

U.S. PATENT DOCUMENTS

2008/0213377 A1* 9/2008 Bhatia ...................... B82Y 5/00
530/300
2021/0330599 A1* 10/2021 Benoit ................ A61K 31/045

FOREIGN PATENT DOCUMENTS

WO WO 2018/213631 A1 * 11/2018 ............ A61K 47/50

OTHER PUBLICATIONS

Arafa et al.; "Preparation of PLGA-Chitosan Based Nanocarriers for Enhancing Antibacterial Effect of Ciprofloxacin in Root Canal Infection"; Drug Delivery; vol. 27, No. 1, pp. 26-39. Published in 2020.*

* cited by examiner

*Primary Examiner* — Jeffrey T. Palenik
(74) *Attorney, Agent, or Firm* — Hodgson Russ LLP

(57) ABSTRACT

The present disclosure provides nanoparticles comprising delmopinol and/or the sodium salt of delmopinol. Also provided are methods of using the nanoparticles and methods of making the nanoparticles.

20 Claims, 4 Drawing Sheets

A

B

DELMOPINOL AND DELMOPINOL SALT CONTAINING NANOPARTICLES AND USES THEREOF

CROSS REFERENCE TO RELATED APPLICATIONS

This application claims priority to U.S. Provisional Application No. 63/322,901, filed Mar. 23, 2022, the disclosure of which is incorporated herein by reference.

BACKGROUND OF THE DISCLOSURE

Biofilms are a microbial community made up of one or more microorganisms that can grow on various surfaces. Microbial colonies that form the biofilms uses extremely unique methods to attach to surfaces and produce extremely resistant matrices. This is achieved by releasing polysaccharides, lipids, nucleic acids, and proteins to form a protective layer surrounding the bacterium. Infections that follow when biofilms lead to devastating diseases like infective endocarditis, pneumonia in cystic fibrosis and repeated urinary tract infection (UTI) leads to approximately 1.7 million hospital-acquired infections annually in the United States, incurring an annual economic burden of approximately 11 billion dollars.

Indwelling Foley catheter is a conduit for bacteria to find entry into the urinary tract and establish colonization of a patient's bladder within three days of their introduction. Bacteria may ascend into the tract via either the external or internal surface of the catheter. Most often microorganisms colonize the external catheter surface by adherence thereby creating a biofilm, usually by the capillary action. Biofilms are complex structures that include bacteria, host cells and cellular by-products and can develop on human, animal and plant tissues. Biofilms can also grow on medical devices and implants that have been placed during the routine medical procedures. Biofilms formation subsequent to insertion of the Foley catheters for different medical indications are proposed to be a primary mechanism in the development of catheter associated urinary tract infections including some other diseases. Bacteria tend to ascend early after catheter insertion. This suggests a lack of asepsis during initial insertion. Intraluminal bacterial accession tend to be introduced when opening the otherwise closed urinary drainage system. Microbes ascend from the urine collection bag into the bladder via reflux. Any breach or damage to urinary bladder mucosa facilitates biofilm formation on this surface. Biofilms are constituted by cells irreversibly attached to a surface or to each other and embedded in a matrix of extracellular polymeric substances (EPS). On similar lines, biofilms may form on central venous lines, stents, cerebral shunts, prosthesis, artificial joints etc. and lead to infections.

Biofilm may have a single microorganism or mixtures of many species of bacteria as well as fungi, algae, yeasts, along with dead cells. Only 10% of a biofilm includes the microbial mass with the other 90% contributed by the extracellular matrix, a great deal of which is composed of water. The consistency of biofilms is that of "stiff water" despite the slimy texture they display when viewed macroscopically. An exopolysaccharide production is increased, which could form an exo-polymer slime layer and protect the bacteria against a variety of antimicrobial agents as well as against host attack. Biofilms grow in environment where there is a combination of moisture, nutrients, and a surface. Biofilms are responsible for about 60% of all microbial infections in the human body. Common problems such as urinary tract infection, catheter associated urinary tract infections, ear infections, teeth and gum infections and contact lenses coatings could all be subsequent to biofilms formed at different anatomical locations.

*E. coli* is most commonly responsible pathogen for nosocomial infections. *Pseudomonas, Enterococcus* species, *Staphylococcus aureus*, coagulase-negative staphylococci, *Enterobacter* species and yeast also are known to cause infection. *Proteus* and *Pseudomonas* species are the organisms most commonly associated with biofilm growth on catheters. Risk factors for bacteriuria in patients who are catheterized include longer duration of catheterization, colonization of the drainage bag, diabetes, absence of antibiotics, female gender, renal insufficiency, errors in catheter care, prolonged catheterization in the hospital course and immuno-compromised or debilitated states. Prolonged antibiotic treatment for 3-14 days on an average as per the studies have shown to reduce the risk of UTI.

The bacteria present in the oral cavity are also present in the genitourinary tract. As explained, although different bacteria will contribute to different components in the biofilm, individually, each one will be producing the same matrix at different anatomic locations. Mechanism of formation of biofilms at different anatomic locations remains the same. The biofilm will aim at a common goal everywhere- to hold bacteria in the biofilm itself and lead to colonization and resistant infections.

All these infections have a chronic component in common and are very persistent and highly resistant to antimicrobial treatments and host defense. Acute infections can be removed following a short treatment course of antibiotics. Biofilms induced infections however are usually never completely eliminated and are responsible for recurrent infections. Bacteria in the biofilms could be one thousand times more resistant to antibiotics than the same bacteria grown in liquid medium. It is very difficult to clean the biofilms due to the strength they adhere with the surfaces. This is because the cells produce extracellular polymeric substances (EPS) which form very adhesive gels with water and binds them to the surface. Many biofilms are quite harmful and must be treated or controlled. Despite extensive research into the nature of biofilms, much about the EPS remains a mystery The approaches to deal with biofilm-associated problems include 1) irrigation of the urinary bladder with biofilm dissolving compound. 2) Catheters, stents and prosthesis undergoing creative changes, 2) anti-biofilm formulations coatings of catheter and stents, 3) changes to the materials and architecture of apparatus to help avoid biofilm formation. Additionally, delineating the urinary microbiome of catheter-associated microbes can also provide potential solutions. Despite multiple available options there is still no headway on approaches to effectively solve the biofilm formation on implanted devices.

BRIEF SUMMARY OF THE DISCLOSURE

The present disclosure provides nanoparticles comprising delmopinol and/or the sodium salt of delmopinol. Also provided are methods of using the nanoparticles and methods of making the nanoparticles.

In an aspect, the present disclosure provides nanoparticles comprising delmopinol. The nanoparticles may comprise one or more additional drugs, such as, for example, antibiotics.

The nanoparticles may be core-shell nanoparticles. The core of the nanoparticle may comprise poly(lactic-co-glycolic acid) (PLGA) and the shell may comprise chitosan. At physiological pH, it is expected that the PLGA is anionic and the chitosan is cationic. The nanoparticles may be unilamellar, bilamellar, or multilamellar. The cationic shell is desirable because the resulting nanoparticles may be more effectively taken up by cells and then it further reduces elimination from circulation by reticuloendothelial system (RES). Additionally, the nanoparticles may facilitate the gradual release of any cargo (e.g., delmopinol, its salts, and/or antibiotics) associated with or encapsulated by nanoparticle. In various embodiments, the surface of the nanoparticles are smooth. In various embodiments, the nanoparticles have a spherical morphology. In various embodiments, the nanoparticles may have an aqueous compartment. Without intending to be bound by any particular theory, it is considered that the layer or space between the chitosan and PLGA is hydrophilic.

In an aspect, the present disclosure provides methods of making and loading nanoparticles.

In an aspect, the present disclosure provides methods of using the nanoparticles. For example, the nanoparticles are disposed on a surface or impregnated into a surface to provide delayed and/or sustained release of the delmopinol, delmopinol salt, and/or antibiotic from the nanoparticles.

In an aspect, the present disclosure provides articles of manufacture. The articles of manufacture may be medical devices or surgical devices that are typically known to be prone to the formation of biofilms. The articles of the present disclosure reduce the growth and/or inhibit the growth of biofilms.

Articles of the present disclosure may be impregnated with nanoparticles of the present disclosure that comprise delmopinol, delmopinol salts, and/or additional cargo (e.g., antibiotics). In various examples, the nanoparticles further comprise peptides (e.g., targeting peptides). Examples of articles include, but are not limited to, catheters, shunts, prosthesis, dental chair lines, stents, and the like.

BRIEF DESCRIPTION OF THE FIGURES

For a fuller understanding of the nature and objects of the disclosure, reference should be made to the following detailed description taken in conjunction with the accompanying figures.

DETAILED DESCRIPTION OF THE DISCLOSURE

Figure 1:
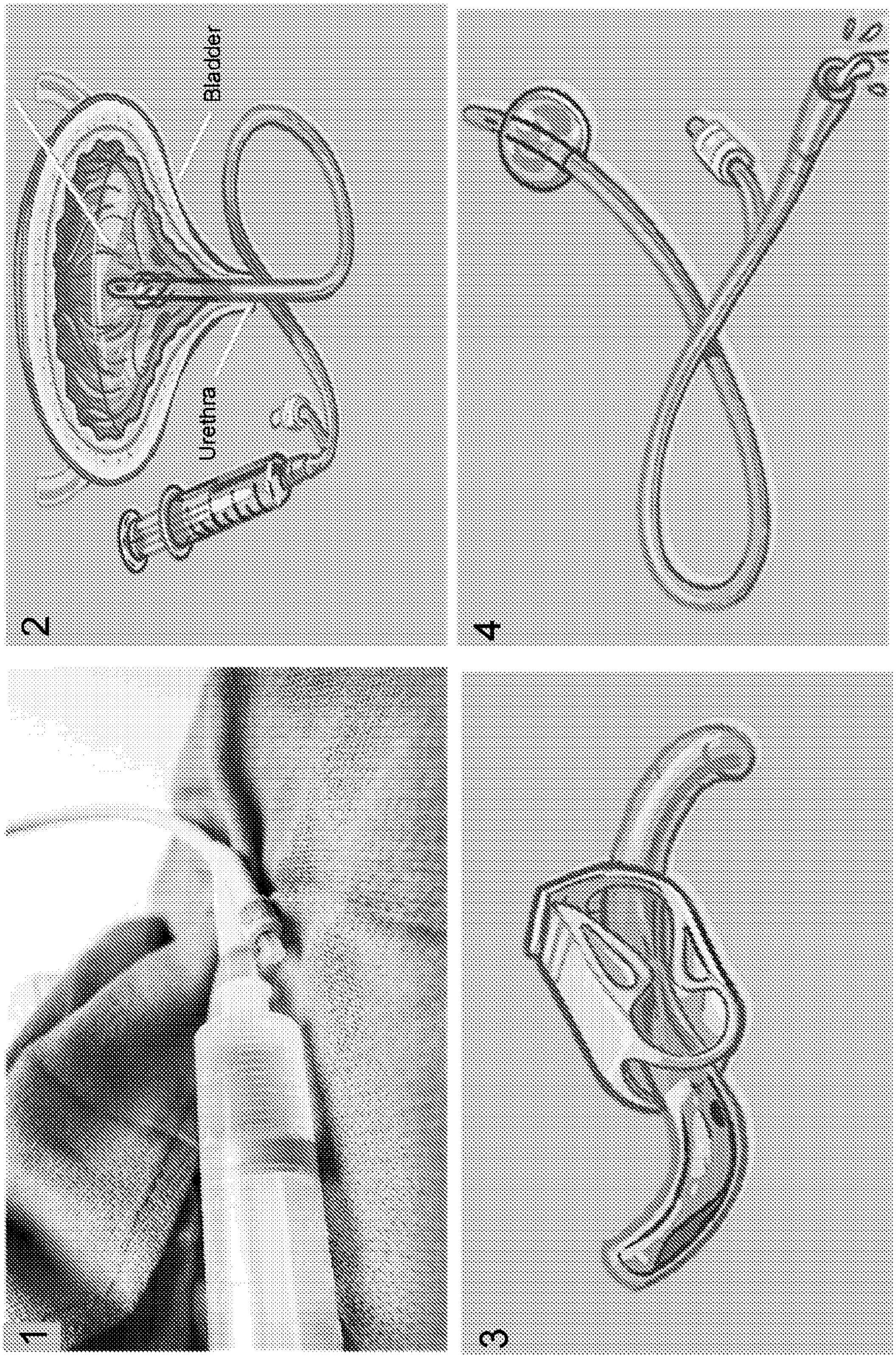
FIG. 1 shows administration of biofilm dissolving compound encapsulated in nanoparticle into the bladder. Biofilm dissolving compound into urinary bladder. The administration involves the following steps: (1) Biofilm dissolving formulation loaded syringe: syringe filled with biofilm dissolving compound is attached to the irrigation channel of the Foley catheter (B) the Foley catheter is inserted through the urethra and the solution containing the biofilm dissolving compound is injected, (3) the catheter is clamped for the nanoparticle solution to remain inside and (4) after about 15 minutes the catheter is unclamped, the fluid is drained and the catheter is removed.
Figure 2:
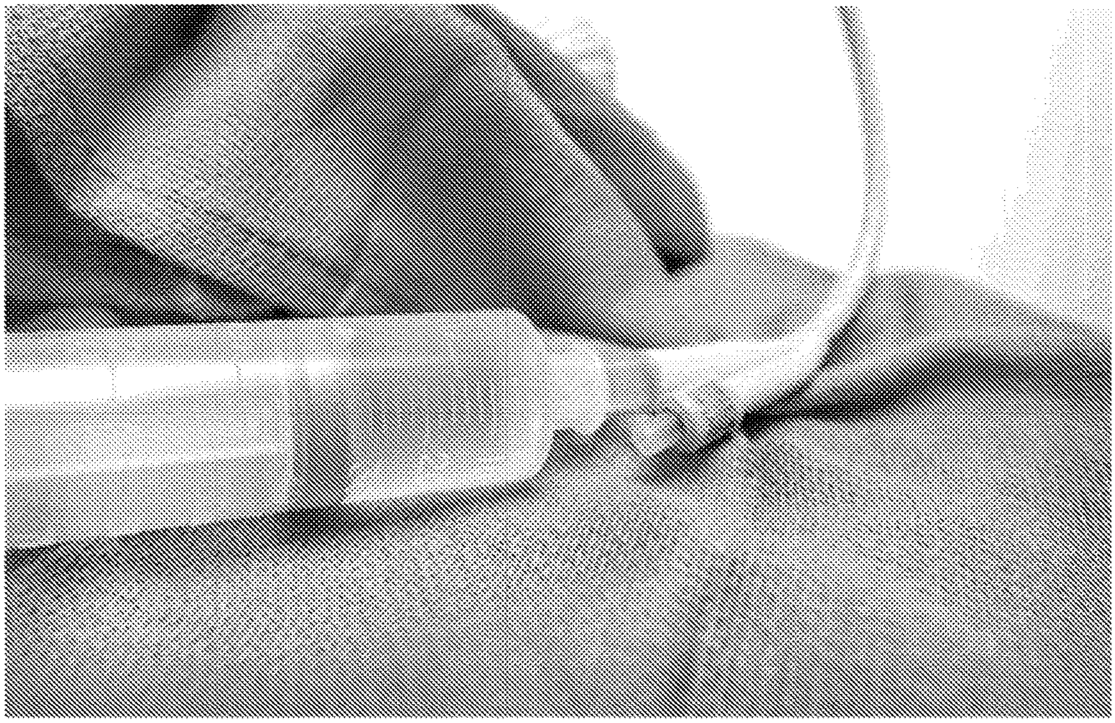
FIG. 2 shows administration of biofilm dissolving compound into urinary bladder. (A) syringe loaded with solution (B) the direct insertion and administration of the solution into the bladder via the urethra.
Figure 2:
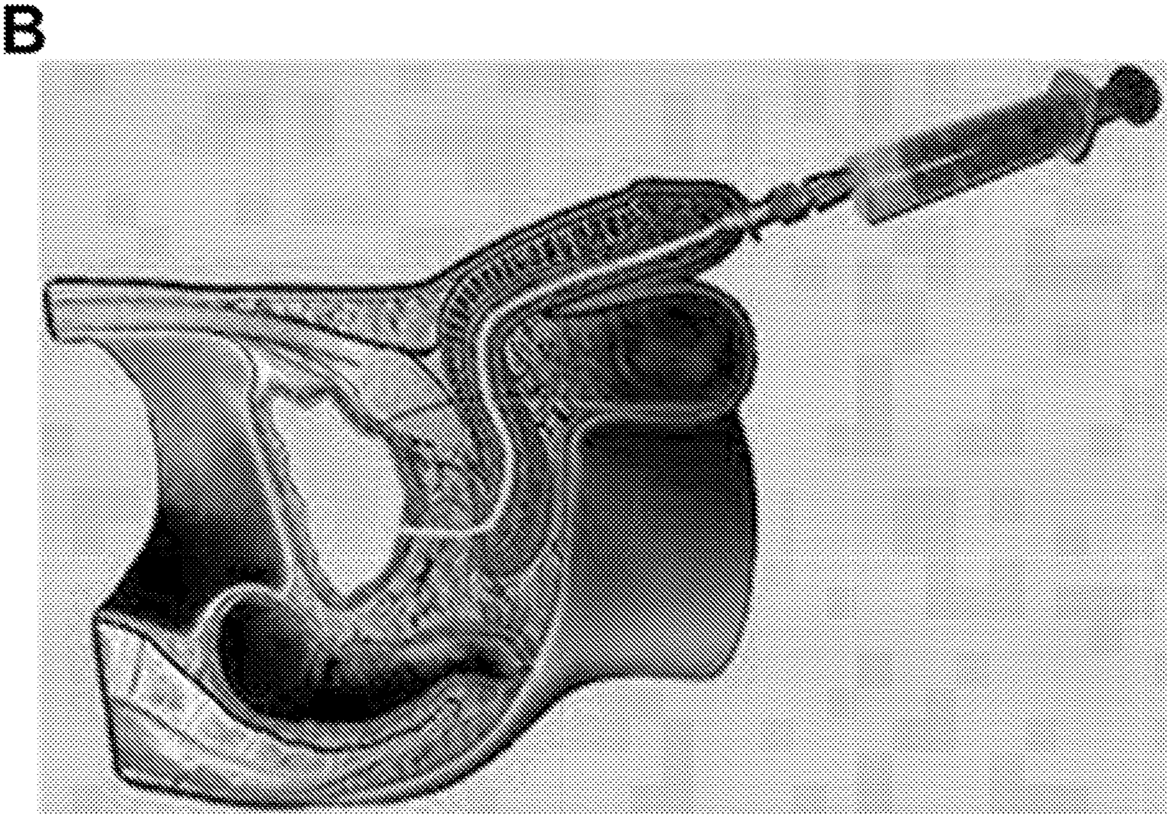

Although claimed subject matter will be described in terms of certain embodiments, other embodiments, including embodiments that do not provide all of the benefits and features set forth herein, are also within the scope of this disclosure. Various structural, logical, and process step may be made without departing from the scope of the disclosure.

All ranges provided herein include all values that fall within the ranges to the tenth decimal place, unless indicated otherwise.

As used in this disclosure, the singular forms "a", "an", and "the" include plural references and vice versa, unless the context clearly dictates otherwise. Thus, for example, references to "the method" includes one or more methods, and/or steps of the type described herein.

The present disclosure provides nanoparticles comprising delmopinol and/or the sodium salt of delmopinol. Also provided are methods of using the nanoparticles and methods of making the nanoparticles.

In an aspect, the present disclosure provides nanoparticles comprising delmopinol. The nanoparticles may comprise one or more additional drugs, such as, for example, antibiotics.

The nanoparticles may be core-shell nanoparticles. The core of the nanoparticle may comprise poly(lactic-co-glycolic acid) (PLGA) and the shell may comprise chitosan. At physiological pH, it is expected that the PLGA is anionic and the chitosan is cationic. The nanoparticles may be unilamellar, bilamellar, or multilamellar. The cationic shell is desirable because the resulting nanoparticles may be more effectively taken up by cells and then it further reduces elimination from circulation by reticuloendothelial system (RES). Additionally, the nanoparticles may facilitate the gradual release of any cargo (e.g., delmopinol, its salts, and/or antibiotics) associated with or encapsulated by nanoparticle. In various embodiments, the surface of the nanoparticles are smooth. In various embodiments, the nanoparticles have a spherical morphology. In various embodiments, the nanoparticles may have an aqueous compartment. Without intending to be bound by any particular theory, it is considered that the layer or space between the chitosan and PLGA is hydrophilic.

Various types of PLGA may be used. For example, the PLGA is 50:50 lactide:glycolide PLGA. Further various weights of PLGA may be used. For example, the PLGA may have a molecular weight of 30,000-60,000 Da, including all 0.1 Da values and ranges therebetween. In various examples, the PLGA 50:50 is ester terminated and has a molecular weight of 24-38 kDa.

Chitosan of various molecular weights can be used. For example, the chitosan has an average molecular weight of 5,000 Da. In various other examples, the molecular weight of the chitosan is 100,000 to 2,000,000, has a viscosity that is less than or equal to 800 mPa s, and the deacetylation is greater than or equal to 80%.

The nanoparticles comprise delmopinol and/or a salt of delmopinol (e.g., a metal salt, such as, for example, a sodium salt or calcium salt of delmopinol). Delmopinol has the following structure:

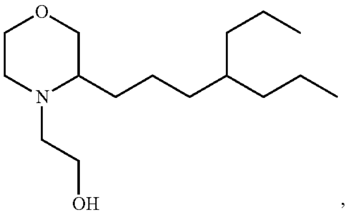 [SMILES: CCCC(CCC)CCCC1COCCN1CCO]

, and the sodium salt of delmopinol has the following structure:

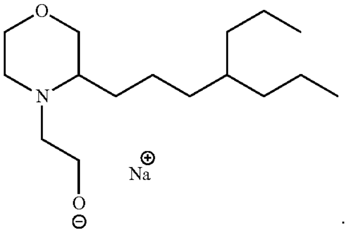 [SMILES: CCCC(CCC)CCCC1COCCN1CC[O-] ; [Na+]]

.

Delmopinol and its sodium salt may be made by the following synthetic route:

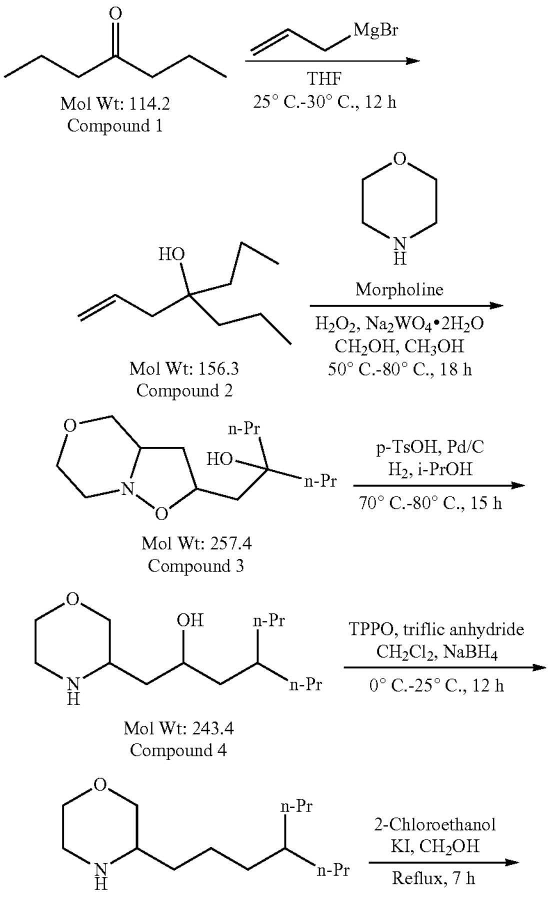

Mol Wt: 114.2
Compound 1

Mol Wt: 156.3
Compound 2

Mol Wt: 257.4
Compound 3

Mol Wt: 243.4
Compound 4

Mol Wt: 227.4
Compound 5

-continued

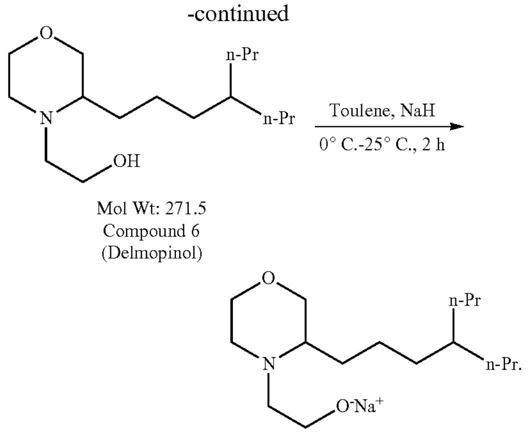

Mol Wt: 271.5
Compound 6
(Delmopinol)

Mol Wt: 294.5
Compound 7
(Delmopinol Sodium salt)

The delmopinol and/or its salt may be associated with, attached to, encapsulated by, or partially encapsulated by the nanoparticles. Without intending to be bound by any particular theory, it is considered that delmopinol and its salts (e.g., sodium salt of delmopinol) can remove biofilms and inhibit formation of biofilms. In various examples, the nanoparticles have an encapsulation efficiency of about 60% or less. In various examples, the nanoparticles comprise 120 μg of delmopinol and/or its salt. In various examples, the nanoparticles comprise about 120 μg of delmopinol and/or its salt. In various examples, the nanoparticles comprise less than 120 μg of delmopinol and/or its salt.

The nanoparticles of the present disclosure may be used to remove or inhibit the formation of various biofilms. Examples of bacteria from which the biofilms can form include, but are not limited to, *Escherichia Coli, Pseudomonas aeruginosa, Proteus mirabilis, Providencia stuartii, Enterococcus faecalis, Staphylococcus epidermidis, Enterococcus faecalis, Klebsiella Pneumoniae*, and the like.

The nanoparticles may be various sizes. For example, a nanoparticle of the present disclosure has a longest linear dimension (e.g., diameter) of 100 to 300 nm, including all nm values and ranges therebetween (e.g., 130 to 235 nm). The nanoparticles may have a desirable size distribution. In various embodiments, the nanoparticles do not have a longest linear dimension exceeding 200 nm. In various other embodiments, the nanoparticles do not have a longest linear dimension exceeding 250 nm (e.g., 235 nm). Without intending to be bound by any particular theory, it is considered the range and the variation of size of the nanoparticles is due to due to the interaction between chitosan molecules as the chitosan amount is increased.

In various examples, the nanoparticles further comprise additional cargo. The nanoparticles may comprise a plurality of different cargo. The additional cargo may be antibiotics. Non-limiting examples of types of antibiotics include penicillins, cephalosporins, tetracyclines, aminoglycosides, macrolides, macrolides, sulfonamides, quinolones, lincosamides, glycopeptides, and the like. In various examples, the cargo may be flavanoids type compounds, such as Quercetins and Polyphenols. Additional examples of cargo include quorum sensing inhibitors like N-(4-[4-fluoroanilno]butanoyl)-L-homoserine lactone (FABHL) and N-(4-[4-chloroanalino]butanoyl)-L-homoserine lactone (CABHL).

Examples of antibiotics include, but are not limited to, phenoxymethylpenicillin, dicloxacillin, ampicillin, facillin, oxacillin, penicillin V, penicillin G, flucloxacilline, amoxicillin, cefaclor, cefadroxil, cephalexin, cefazolin, cefuroxime, cefixime, cefoxitin, ceftriaxone, tetracycline, doxycycline, minocycline, sarecycline, lymecycline, gentamicin, tobramycin, amikacin, planomycin, streptomycin, neomycin, paromomycin, erythromycin, azithromycin, clarithromycin, clindamycin, fidaxomicin, roxithromycin, trimethoprim, co-trimoxazole, metronidazole, tinidazole, ciprofloxacin, levofloxacin, norfloxacin, ofloxacin, moxifloxacin, nitrofurantoin, sulfamethoxazole, sulfasalazine, sulfacetamide, sulfadiazine silver, vancomycin, dalbavancin, oritavancin, telavancin, and the like. Other antibiotics are known in the art and are contemplated for use with the nanoparticles described herein. In various embodiments, the nanoparticles hold 500 μg of additional cargo (e.g., antibiotic). In various embodiments, the nanoparticles hold about 500 μg of additional cargo (e.g., antibiotic). In various embodiments, the nanoparticles hold less than or equal to 500 μg of additional cargo (e.g., antibiotic).

In various examples, the nanoparticles further comprise a peptide. The peptide may be a targeting peptide, which directs the nanoparticle to a specific region of interest (e.g., a tissue). For example, the peptide may be 3 to 20 amino acids long (e.g., 3, 4, 5, 6, 7, 8, 9, 10, 11, 12, 13, 14, 15, 16, 17, 18, 19, or 20 amino acids long). Examples of targeting peptide are known in the art. The peptide may be covalently attached to the nanoparticle or may be non-covalently attached to the nanoparticle.

In various examples, the present disclosure provides different populations of nanoparticles. For example, first nanoparticle population may comprise nanoparticles comprising delmopinol and/or a delmopinol salt (e.g., sodium delmopinol salt); a second nanoparticle population may comprise nanoparticles comprising cargo (e.g., one or more additional antibiotics); or a third population comprising delmopinol and/or a delmopinol salt (e.g., sodium delmopinol salt) and additional cargo (e.g., one or more additional antibiotics). A composition may comprise one or more or all of these populations. In various examples, one or more or all of the nanoparticles of each of these populations may further comprise nanoparticles comprising one or more peptides as described herein. A composition of the present disclosure may comprise one or more of the populations described herein.

In various examples, the nanoparticles may have functional groups on the nanoparticle surface that may be used to conjugate cargo (e.g., antibiotics) or peptides. The functional groups may be functional groups typically used in conjugation reactions. For example, the functional group may be nucleophilic (e.g., an amine, alcohol, thiol, or the like) or electrophilic (e.g., an activated ester, ester, carboxylic acid, anhydride, olefin, or the like) to facilitate a substitution reaction (e.g., via an acylation reaction). In various other examples, the functional group may be a alkyne or azide used to facilitate a “click reaction.” Other conjugation methods may be used and are known in the art.

In an aspect, the present disclosure provides methods of making and loading nanoparticles.

Various methods may be used to make a nanoparticle of the present disclosure and various methods may be used to load a nanoparticle of the present disclosure. For example, the nanoparticles may be formed via water-oil-water emulsion techniques or by precipitation (e.g., nanoprecipitation) via high gravity rotating packed bed (RPB) reactors.

For example, the nanoparticles may be produced by an emulsion technique. The PLGA may be dissolved in an organic solvent (e.g., dichloromethane (DCM)) and mixed with water. Delmopinol and/or delmopinol salt (e.g., delmopinol sodium salt) and/or additional cargo (e.g., one or more antibiotics) may be added to this mixture. The mixture is then cooled (e.g., cooled to 4° C.) and sonicated, followed by the addition of sodium acetate, polyvinyl alcohol, and chitosan. This mixture may then be stirred and centrifuged. The supernatant is then removed and the nanoparticles may be isolated.

In other embodiments, the nanoparticles may be produced by precipitation (e.g., nanoprecipitation) using a high gravity RPB reactor. A first mixture, comprising PLGA and delmopinol and/or delmopinol salt and/or additional cargo (e.g., one or more antibiotics) in an organic solvent (e.g., acetone) is prepared. Separately, a second mixture comprising a surfactant (e.g., Poloxamer® 188), acetic acid, chitosan, and water is prepared. The two mixtures are pumped (e.g., pumped at different rates (e.g., the first mixture at a flow rate of 15 mL/min and the second mixture at a flow rate of 300 mL/min)) into an RPB reactor. The nanoparticles are then isolated from the supernatant (e.g., via lyophilization).

In an aspect, the present disclosure provides methods of using the nanoparticles. For example, the nanoparticles are disposed on a surface or impregnated into a surface to provide delayed and/or sustained release of the delmopinol, delmopinol salt, and/or antibiotic from the nanoparticles.

For examples, various articles may have surfaces suitable for impregnation of the nanoparticles or surfaces upon which the nanoparticles may be disposed. Such articles include, but are not limited to, catheters (e.g., Foley catheters), shunts, prosthesis, dental chair lines, stents, and the like. In various examples, the articles do not comprise metal. Articles may comprise drainage tubes having interior and exterior surfaces. For example, at least a portion of the interior surface of a catheter or the catheter of a stent are impregnated with the nanoparticles of the present disclosure or have the nanoparticles disposed thereon (coated). In various other examples, the exterior surface of a catheter or the catheter of the stent may be impregnated or have nanoparticles disposed thereon (e.g., coated).

In various embodiments, nanoparticle suspensions may be coated on an article (e.g., catheter) by perpendicularly spraying the article (e.g., the silicon tubes of the catheter) to by air pump spray gun with the flow rate of 0.2 mL/s. The article may be dried under airflow and repeated for homogenous coating. In various examples, the coating of nanoparticles may be around 100 nm.

The nanoparticles may provide delayed and/or sustained release of delmopinol, delmopinol salt, and/or antibiotic from the impregnated surface or the surface upon which the nanoparticles are disposed. For example, the release may occur over 14 to 42 days, including all integer day values and ranges therebetween.

The nanoparticles may be impregnated into the article by various methods. For example, during fabrication of a drainage tube of a catheter, loaded nanoparticles (e.g., loaded with delmopinol, its salt (e.g., sodium salt), and/or one or more additional cargo) compositions may be mixed with raw material of which the drainage tube is comprised (e.g., polyethylene, polypropylene, polyurethane, polycarbonate, polyethermide, pebax, nylons, or the like) prior to pouring the raw material into a vulcanization mold. The drainage tube is then formed and comprises the loaded nanoparticles. In other embodiments, the nanoparticles are disposed (e.g., coated) onto at least a portion of the interior and/or exterior surface of a drainage tube of a catheter. The disposed nanoparticles may be in a thin film or in a hydrogel or other coating. For example, the nanoparticles may be sprayed onto the desired surface.

In an aspect, the present disclosure provides articles of manufacture. The articles of manufacture may be medical devices or surgical devices that are typically known to be prone to the formation of biofilms. The articles of the present disclosure reduce the growth and/or inhibit the growth of biofilms.

Articles of the present disclosure may be impregnated with nanoparticles of the present disclosure that comprise delmopinol, delmopinol salts, and/or additional cargo (e.g., antibiotics). In various examples, the nanoparticles further comprise peptides (e.g., targeting peptides). Examples of articles include, but are not limited to, catheters, shunts, prosthesis, dental chair lines, stents, and the like.

In other embodiments, the articles have at least a portion of a surface that has nanoparticles comprising delmopinol, delmopinol salts, and/or additional cargo disposed thereon.

The steps of the method described in the various embodiments and examples disclosed herein are sufficient to carry out the methods of the present invention. Thus, in an embodiment, the method consists essentially of a combination of the steps of the methods disclosed herein. In another embodiment, the method consists of such steps.

The following Statements provide various embodiments of the present disclosure.

Statement 1. A core-shell nanoparticle comprising a poly (lactic-co-glycolic acid) (PLGA) core and a chitosan shell, wherein the core-shell nanoparticle further comprises delmopinol and/or the sodium salt of delmopinol.

Statement 2. A core-shell nanoparticle according to Statement 1, wherein the PLGA is 50:50 lactide:glycolide PLGA with a molecular weight of 30-60 kDa.

Statement 3. A core-shell nanoparticle according to Statement 1 or Statement 2, wherein the chitosan of the chitosan shell has an average molecular weight of 5 kDa.

Statement 4. A core-shell nanoparticle according to any one of the preceding Statements, wherein the longest linear dimension of the nanoparticle is less than or equal to 200 nm.

Statement 5. A core-shell nanoparticle according to any one of the preceding Statements, further comprising one or more additional cargo.

Statement 6. A core-shell nanoparticle according to Statement 5, wherein the one or more additional cargo is one or more antibiotics.

Statement 7. A core-shell nanoparticle according to Statement 6, wherein the antibiotic is chosen from penicillins, cephalosporins, tetracyclines, aminoglycosides, macrolides, macrolides, sulfonamides, quinolones, lincosamides, glycopeptides, and the like, and combinations thereof.

Statement 8. A core-shell nanoparticle according to Statement 6 or Statement 7, wherein the antibiotic is chosen from phenoxymethylpenicillin, dicloxacillin, ampicillin, facillin, oxacillin, penicillin V, penicillin G, flucloxacilline, amoxicillin, cefaclor, cefadroxil, cephalexin, cefazolin, cefuroxime, cefixime, cefoxitin, ceftriaxone, tetracycline, doxycycline, minocycline, sarecycline, lymecycline, gentamicin, tobramycin, amikacin, planomycin, streptomycin, neomycin, paromomycin, erythromycin, azithromycin, clarithromycin, clindamycin, fidaxomicin, roxithromycin, trimethoprim, co-trimoxazole, metronidazole, tinidazole, ciprofloxacin, levofloxacin, norfloxacin, ofloxacin, moxifloxacin, nitrofurantoin, sulfamethoxazole, sulfasalazine, sulfacetamide, sulfadiazine silver, vancomycin, dalbavancin, oritavancin, telavancin, and the like, and combinations thereof.

Statement 9. A core-shell nanoparticle according to any one of the preceding Statements, further comprising a peptide.

Statement 10. A core-shell nanoparticle according to Statement 9, wherein the peptide is a targeting peptide.

Statement 11. A composition comprising a first population of nanoparticles comprising core-shell nanoparticles comprising a poly(lactic-co-glycolic acid) (PLGA) core and a chitosan shell, wherein the core-shell nanoparticle further comprises delmopinol and/or the sodium salt of delmopinol.

Statement 12. A composition according to claim 11, further comprising a second population of nanoparticles comprising core-shell nanoparticles comprising a poly(lactic-co-glycolic acid) (PLGA) core and a chitosan shell, wherein the core-shell nanoparticle further comprises one or more cargo.

Statement 13. A composition according to Statement 11 or Statement 12, further comprising a third population of nanoparticles core-shell nanoparticles comprising a poly(lactic-co-glycolic acid) (PLGA) core and a chitosan shell, wherein the core-shell nanoparticle further comprises one or more cargo molecules and delmopinol and/or the sodium salt of delmopinol.

Statement 14. A composition according to Statement 12 or Statement 13, wherein the one or more additional cargo is one or more antibiotics.

Statement 15. A composition according to Statement 14, wherein the antibiotic is chosen from penicillins, cephalosporins, tetracyclines, aminoglycosides, macrolides, macrolides, sulfonamides, quinolones, lincosamides, glycopeptides, and the like, and combinations thereof.

Statement 16. A composition according to Statement 14 or Statement 15, wherein the antibiotic is chosen from phenoxymethylpenicillin, dicloxacillin, ampicillin, facillin, oxacillin, penicillin V, penicillin G, flucloxacilline, amoxicillin, cefaclor, cefadroxil, cephalexin, cefazolin, cefuroxime, cefixime, cefoxitin, ceftriaxone, tetracycline, doxycycline, minocycline, sarecycline, lymecycline, gentamicin, tobramycin, amikacin, planomycin, streptomycin, neomycin, paromomycin, erythromycin, azithromycin, clarithromycin, clindamycin, fidaxomicin, roxithromycin, trimethoprim, co-trimoxazole, metronidazole, tinidazole, ciprofloxacin, levofloxacin, norfloxacin, ofloxacin, moxifloxacin, nitrofurantoin, sulfamethoxazole, sulfasalazine, sulfacetamide, sulfadiazine silver, vancomycin, dalbavancin, oritavancin, telavancin, and the like, and combinations thereof.

Statement 17. A composition according to any one of Statements 11-16, wherein one or more of the nanoparticles further comprise a peptide.

Statement 18. A composition according to Statement 17, wherein the peptide is a targeting peptide.

Statement 19. A container comprising one or more nanoparticles according to any one of Statements 1-10 or a composition according to any one of Statements 11-18.

Statement 20. An article impregnated with a nanoparticle according to any one of Statements 1-10 or a composition according to any one of Statements 11-18.

Statement 21. An article according to Statement 20, wherein the article is a catheter or stent.

Statement 22. An article according to Statement 20 or Statement 21, wherein the article does not comprise metal.

Statement 23. An article according to Statement 21 or Statement 22, wherein the article is a catheter and an interior surface and/or exterior surface of the catheter is impregnated with the nanoparticles or the composition.

Statement 24. An article having a surface with a nanoparticle according to any one of Statements 1-10 or a composition according to any one of Statements 11-18 disposed thereon.

Statement 25. An article according to Statement 24, wherein the article is a catheter or stent.

Statement 26. An article according to Statement 24 or Statement 25, wherein the article does not comprise metal.

Statement 27. An article according to Statement 25 or Statement 26, wherein the article is a catheter and an interior surface and/or exterior surface of the catheter has the nanoparticles or the composition disposed thereon.

Statement 28. An article according to any one of Statements 24-27, wherein the nanoparticles or compositions are applied via spray.

The following examples are presented to illustrate the present disclosure. They are not intended to be limiting in any matter.

Example 1

This example provides a description of nanoparticles of the present disclosure and methods of making the nanoparticles.

A sustained release of the biofilm removal technology over a time will be ideal to prevent a biofilm to re-establish and ensure effective treatment of infection. The materials used in the fabrication of this nanoparticle are FDA approved and in preclinical studies did not show any dose-related toxicity or discomfort. This nanoparticle can comprise poly (lactic-co-glycolic acid) (PLGA) nanocarriers coated with chitosan (CS) with the biofilm dissolving compound, Delmopinol. This biocompatible nanoformulation enables delivery of Delmopinol with sustained removal of the biofilm. Further, this nanoformulaton can further comprise an antibiotic to control the infections by dissolving the biofilm and decrease the collateral toxicity toward bystander normal tissues.

Nanoparticle (NP) Components:

The nanoparticle (NP) is a core-shell architecture-based NP with Poly (lactic-co-glycolic acid) (PLGA) in the core and chitosan (CS) in the shell. PLGA is an FDA approved, biodegradable, biocompatible copolymer and is anionic at physiologic pH. CS is a positively charged linear polysaccharide derived from crustacean shells and is cationic at physiologic pH. CS coating of PLGA core gives the NP an overall positive charge conferring it with the property to be taken up by cells and avoiding being eliminated from circulation by the reticuloendothelial system (RES).

Nanoparticle Synthesis:

The nanoparticles are synthesized using a water-oil-water (w/o/w) emulsion with solvent evaporation. For this purpose, PLGA (50:50, MW 30-54 kDa) (40 mg/ml) will be dissolved in methylene chloride (MC) and added to 100 μl of distilled water (DDW). Drug (Delmopinol (Del) and/or antibiotic (Ab), in the concentration required is added to this mixture, enabling it to dissolve in the appropriate phase. The mixture will be probe sonicated in a 4° C. bath for 1 min followed by the rapid addition of 0.5 ml of 10 mM sodium acetate pH 4 containing 2.0% polyvinyl alcohol and 1.2 mg CS (MW 5 kDa) and probe sonicated for 1 min. The resulting w/o/w emulsion will be stirred overnight to remove the MC. CS-PLGA nanoparticles were centrifuged at 16,000×g for 10 min, washed twice with deionized water to remove excess surfactant and reconstituted in 1-ml DDW for immediate use. The size, shape, and zeta potential of the nanoparticles will be characterized using dynamic light scattering (DLS) and transmission Electron Microscopy (TEM). The drug concentration within the nanoparticles, both delmopinol and antibiotics will be determined following acetonitrile extraction and analyzed by Ultra performance liquid chromatography-tandem mass spectrometer (UPLC-MS). The PLGA-CS NP can also be sprayed on to the outer surface of a catheter or a stent to release the drug combination at that location.

Example 2

This example provides a description of nanoparticles of the present disclosure and methods of making the nanoparticles.

Nanoparticle (NP) Components:

The nanoparticle (NP) is a core-shell architecture-based NP with Poly (lactic-co-glycolic acid) (PLGA) in the core and chitosan (CS) in the shell. PLGA is an FDA approved, biodegradable, biocompatible copolymer and is anionic at physiologic pH. CS is a positively charged linear polysaccharide derived from crustacean shells and is cationic at physiologic pH. CS coating of PLGA core gives the NP an overall positive charge conferring it with the property to be taken up by cells and avoiding being eliminated from circulation by the reticuloendothelial system (RES).

Nanoparticle Synthesis:

The nanoparticles will be prepared by nanoprecipitation using high gravity rotating packed bed (RPB) reactor. PLGA (200 mg) and the required concentration of Delmopinol and/or Antibiotic (Ab) will be added to acetone (20 mL) to form the organic phase. Separately, Poloxamer 188 (0.3%, w/v), acetic acid (4 mL), and CS (1.2 mg) will be added to deionized water (400 mL) to form the aqueous phase. Next, the organic phase with a flow rate of 15 mL/min and the aqueous phase with a flow rate of 300 mL/min will be pumped into the RPB reactor. The unincorporated drugs will be removed by ultrafiltration centrifugation (12,000 r/min, 15 min) because they stay in the supernatant, which will be discarded. The drug-loaded nanoparticles that remain after the removal of the supernatant will be lyophilized for 48 h for long-term storage or dissolved in DDW for immediate use. The size, shape, and zeta potential of the nanoparticles will be characterized using Dynamic light scattering (DLS) and transmission Electron Microscopy (TEM). The drug concentration within the nanoparticles, both delmopinol and antibiotics will be determined following acetonitrile extraction using Ultra performance liquid chromatography-tandem mass spectrometer (UPLC-MS). Based on what drugs and combinations are used the following populations are expected: PLGA-CS, PLGA-CS-Ab, PLGA-CS-Del, and PLGS-CS-Del-Ab. It is expected that using the nanoparticle fabrication method described above, the co-delivery of Delmopinol, and Ab will show an improved and robust effect to dissolve the biofilm and overcome bacterial resistance.

Example 3

This example provides a description of possible uses of nanoparticles of the present disclosure.

Stent and/or catheter will be pre-treated with the controlled-release formulation for the release of the biofilm dissolving compound (Delmopinol) and Ab and the efficacy of the formulation will be evaluated in pre-clinical models. The controlled release property is achieved by increasing the ratio of CS to PLGA in the synthesis process. For this purpose, either 4 mg, 8 mg or 16 mg CS in deionized water (400 mL) will be used. Because particles smaller than 10 nm are quickly eliminated by renal changes, while those larger than 300 nm are removed from the blood circulation due to the recognition of reticuloendothelial system (RES) this step is very critical. With sufficient positive zeta potential due to the presence of increased amount of CS, the cellular uptake of CS-modified PLGA NPs will be increased and the initial burst release of the encapsulated drugs will be overcome. Additionally, the protonation of the amino group at acidic pH will make CS stick to mucosal layer for sustained release as well.

Example 4

This example provides a description of possible uses of nanoparticles of the present disclosure.

TABLE 1

Size distribution.

| Formulation | Size (nm) | Zeta Potential (meV) | Encapsulation Efficiency (%) |
|---|---|---|---|
| PLGA-CS | 130 ± 9 | +17 ± 1 | N/A |
| PLGA-CS-AB | 159 ± 4 | +17 ± 3 | 61 ± 6 |
| PLGA-CS-Del | 146 ± 9 | +17 ± 4 | 57 ± 6 |
| PLGA-CS-Ab-Del | 185 ± 6 | +17 ± 4 | 67 ± 6 |

CS is chitosan, AB or Ab is antibiotic, Del is delmopinol and/or delmopinol sodium salt.

This example provides a description of possible uses of nanoparticles of the present disclosure.

Two main approaches to coat the external surface of a catheter with the nanoparticle encapsulating biofilm dissolving compound: 1) physiological adsorption and 2) covalent attachment. Covalent attachment was used in the instant Example.

Covalent attachment of the nanoparticle was achieved as follows: initially a thin coating of a plasma polymer layer having surface amine groups was deposited onto a catheter forming a plasma-activated heptyl-amine vapor. Following this, the amine-coated catheter was transferred to an aqueous solution containing poly(acrylic acid) (PAAC) and N-(3-dimethylaminopropyl)-N'-ethylcarbodiimide hydrochloride (EDC) to a generate carboxylated surface. This was followed by creation of an outer surface possessing azide group, achieved by immersing the sample in an aqueous solution of 4-azidoaniline hydrochloride buffered to pH 8.8.

Figure 3:
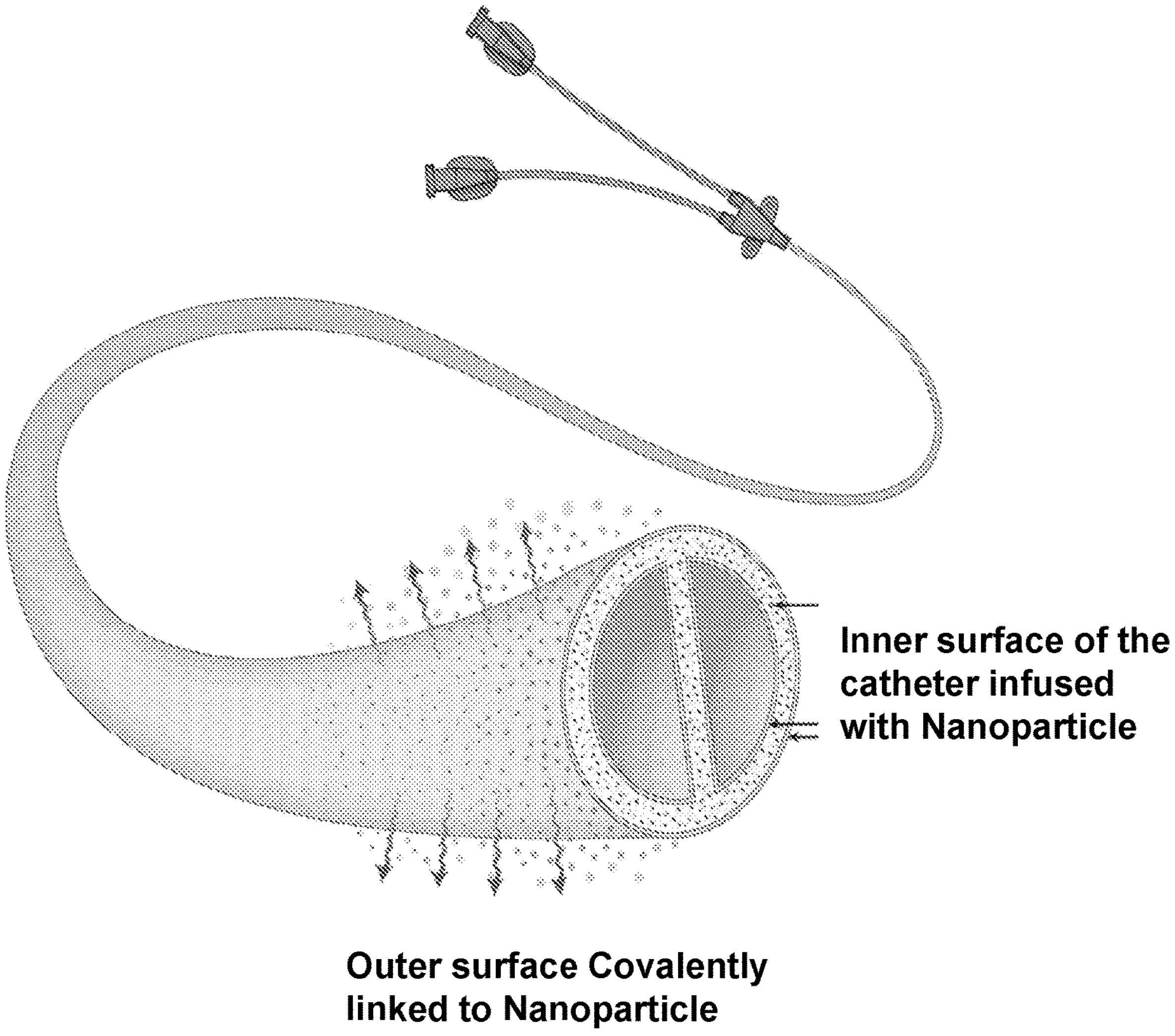
FIG. 3 shows covalently binding nanoparticle containing the biofilm dissolving compound onto styrene of a Foley catheter.
Figure 4:
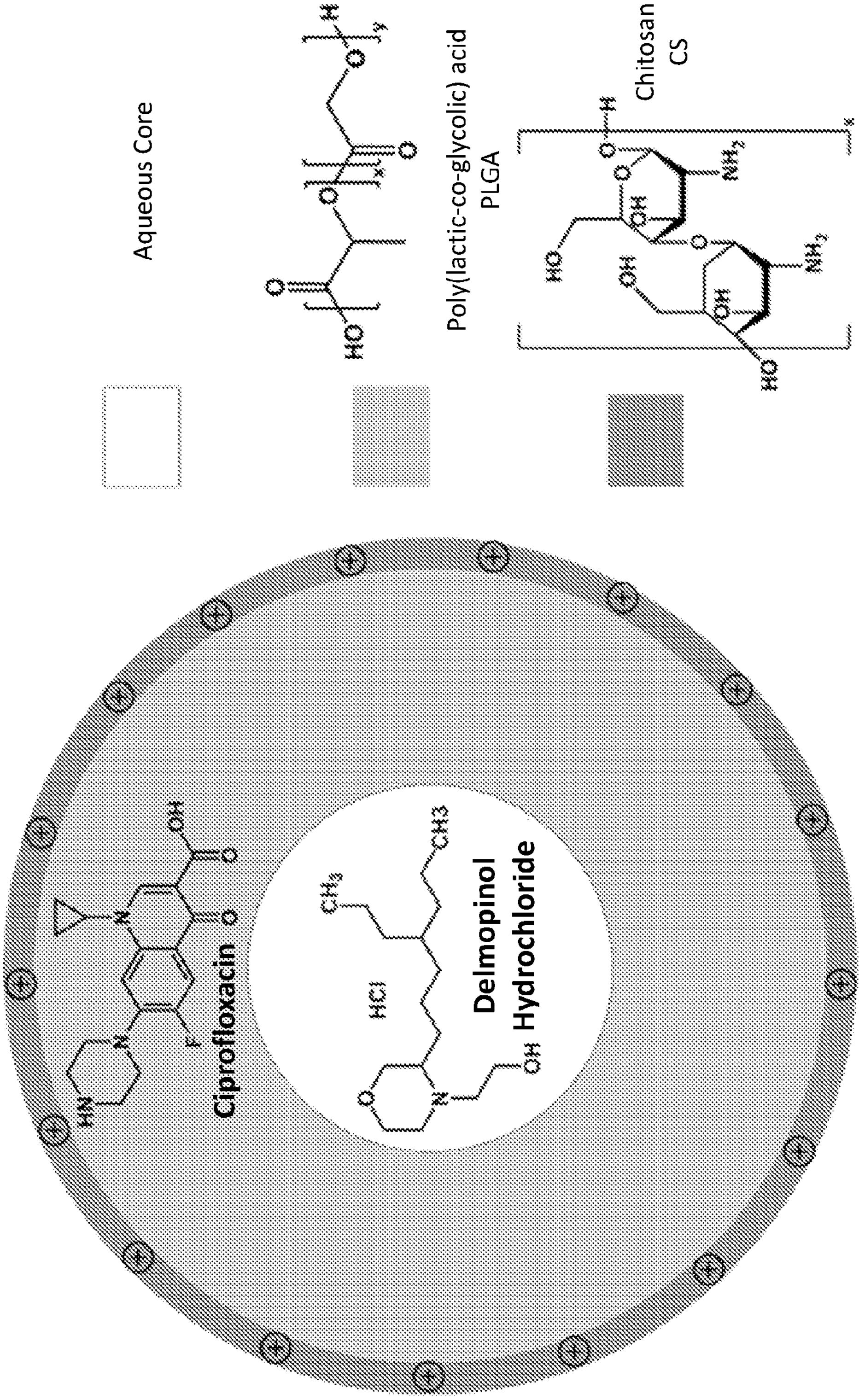
FIG. 4 shows a schematic of a nanoparticle of the present disclosure. The schematic shows ciprofloxacin in the organic layer and a delmopinol salt in the aqueous core.

To the catheter containing azide group our nanoparticle is attached by click chemistry. Ultimately, we end up with a catheter containing infused nanoparticle on the inner side of the catheter and covalently attached nanoparticle on the outside as shown in FIG. 3.

Although the present disclosure has been described with respect to one or more particular embodiments and/or examples, it will be understood that other embodiments and/or examples of the present disclosure may be made without departing from the scope of the present disclosure.

The invention claimed is:

1. A core-shell nanoparticle comprising a poly (lactic-co-glycolic acid) (PLGA) core and a chitosan shell, wherein the core-shell nanoparticle further comprises delmopinol and/or the sodium salt of delmopinol, and, optionally, one or more additional cargo.

2. The core-shell nanoparticle according to claim 1, wherein the PLGA is 50:50 lactide: glycolide PLGA with a molecular weight of 30-60 kDa.

3. The core-shell nanoparticle according to claim 1, wherein the chitosan of the chitosan shell has an average molecular weight of 5 kDa.

4. The core-shell nanoparticle according to claim 1, wherein the longest linear dimension of the nanoparticle is less than or equal to 200 nm.

5. The core-shell nanoparticle according to claim 1, wherein the one or more additional cargo is one or more antibiotics.

6. The core-shell nanoparticle according to claim 5, wherein the one or more antibiotics are chosen from penicillins, cephalosporins, tetracyclines, aminoglycosides, macrolides, macrolides, sulfonamides, quinolones, lincosamides, glycopeptides, and combinations thereof.

7. The core-shell nanoparticle according to claim 5, wherein the one or more antibiotics is chosen from phenoxymethylpenicillin, dicloxacillin, ampicillin, facillin, oxacillin, penicillin V, penicillin G, flucloxacilline, amoxicillin, cefaclor, cefadroxil, cephalexin, cefazolin, cefuroxime, cefixime, cefoxitin, ceftriaxone, tetracycline, doxycycline, minocycline, sarecycline, lymecycline, gentamicin, tobramycin, amikacin, planomycin, streptomycin, neomycin, paromomycin, erythromycin, azithromycin, clarithromycin, clindamycin, fidaxomicin, roxithromycin, trimethoprim, co-trimoxazole, metronidazole, tinidazole, ciprofloxacin, levofloxacin, norfloxacin, ofloxacin, moxifloxacin, nitrofurantoin, sulfamethoxazole, sulfasalazine, sulfacetamide, sulfadiazine silver, vancomycin, dalbavancin, oritavancin, telavancin, and combinations thereof.

8. The core-shell nanoparticle according to claim 1, further comprising a peptide.

9. A composition comprising a first population of nanoparticles comprising core-shell nanoparticles comprising a poly (lactic-co-glycolic acid) (PLGA) core and a chitosan shell, wherein the core-shell nanoparticle further comprises delmopinol and/or the sodium salt of delmopinol, and a second population of nanoparticles comprising core-shell nanoparticles comprising a poly (lactic-co-glycolic acid) (PLGA) core and a chitosan shell, wherein the core-shell nanoparticle further comprises one or more cargo.

10. The composition according to claim 9, wherein the one or more cargo is one or more antibiotics.

11. The composition according to claim 10, wherein the one or more antibiotics is chosen from penicillins, cephalosporins, tetracyclines, aminoglycosides, macrolides, macrolides, sulfonamides, quinolones, lincosamides, glycopeptides, and combinations thereof.

12. The composition according to claim 10, wherein the one or more antibiotics is chosen from phenoxymethylpenicillin, dicloxacillin, ampicillin, facillin, oxacillin, penicillin V, penicillin G, flucloxacilline, amoxicillin, cefaclor, cefadroxil, cephalexin, cefazolin, cefuroxime, cefixime, cefoxitin, ceftriaxone, tetracycline, doxycycline, minocycline, sarecycline, lymecycline, gentamicin, tobramycin, amikacin, planomycin, streptomycin, neomycin, paromomycin, erythromycin, azithromycin, clarithromycin, clindamycin, fidaxomicin, roxithromycin, trimethoprim, co-trimoxazole, metronidazole, tinidazole, ciprofloxacin, levofloxacin, norfloxacin, ofloxacin, moxifloxacin, nitrofurantoin, sulfamethoxazole, sulfasalazine, sulfacetamide, sulfadiazine silver, vancomycin, dalbavancin, oritavancin, telavancin, and combinations thereof.

13. The composition according to claim 9, wherein one or more of the nanoparticles further comprise a peptide.

14. An article impregnated with a nanoparticle according to claim 1.

15. The article according to claim 14, wherein the article is a catheter or stent.

16. The article according to claim 14, wherein the article does not comprise metal.

17. An article having a surface with one or more nanoparticles according to claim 1 disposed thereon.

18. The article according to claim 17, wherein the article is a catheter or stent.

19. The article according to claim 17, wherein the article does not comprise metal.

20. The article according to 17, wherein the nanoparticles or compositions are applied via spray.

* * * * *